(12) United States Patent
Sadat

(10) Patent No.: US 10,207,302 B2
(45) Date of Patent: Feb. 19, 2019

(54) INFECTIOUS WASTE TREATMENT SYSTEM

(71) Applicant: Seyed Morteza Sadat, Tehran (IR)

(72) Inventor: Seyed Morteza Sadat, Tehran (IR)

( * ) Notice: Subject to any disclaimer, the term of this patent is extended or adjusted under 35 U.S.C. 154(b) by 45 days.

(21) Appl. No.: 15/272,449

(22) Filed: Sep. 22, 2016

(65) Prior Publication Data

US 2017/0008051 A1    Jan. 12, 2017

Related U.S. Application Data

(60) Provisional application No. 62/260,486, filed on Nov. 28, 2015.

(51) Int. Cl.
| | | |
|---|---|---|
| *B09B 3/00* | (2006.01) | |
| *A61L 11/00* | (2006.01) | |
| *B65B 55/14* | (2006.01) | |
| *B65B 3/04* | (2006.01) | |
| *B02C 19/00* | (2006.01) | |
| *B02C 18/00* | (2006.01) | |
| *B02C 18/14* | (2006.01) | |
| *B02C 18/18* | (2006.01) | |

(52) U.S. Cl.
CPC .......... *B09B 3/0075* (2013.01); *A61L 11/00* (2013.01); *B02C 18/0084* (2013.01); *B02C 18/142* (2013.01); *B02C 18/146* (2013.01); *B02C 18/182* (2013.01); *B02C 19/0075* (2013.01); *B09B 3/0083* (2013.01); *B65B 3/04* (2013.01); *B65B 55/14* (2013.01)

(58) Field of Classification Search
CPC ... B09B 3/0075; B09B 3/0083; B02C 18/182; B02C 18/146; B02C 18/142; B02C 18/0084; B02C 19/0075; B65B 55/14; B65B 3/04; A61L 11/00
See application file for complete search history.

(56) References Cited

U.S. PATENT DOCUMENTS

| | | | | |
|---|---|---|---|---|
| 5,155,975 | A * | 10/1992 | Knowler | B02C 18/14 141/272 |
| 5,425,925 | A | 6/1995 | Kline et al. | |
| 5,427,321 | A * | 6/1995 | Takahashi | B02C 18/0007 241/100 |
| 5,538,193 | A * | 7/1996 | Takahashi | B02C 18/0007 241/100 |
| 5,864,919 | A * | 2/1999 | Pineda | A47L 5/14 15/339 |
| 8,454,795 | B1 * | 6/2013 | Henderson | E04B 1/74 162/141 |

(Continued)

FOREIGN PATENT DOCUMENTS

WO    2013050822 A1    4/2013

*Primary Examiner* — Regina M Yoo
(74) *Attorney, Agent, or Firm* — Bajwa IP Law Firm; Haris Zaheer Bajwa

(57) ABSTRACT

A method and apparatus for infectious waste treatment. First, the infectious waste may be shredded into a mixture of liquid and shredded solid waste, then the mixture may be poured into a plurality of perforated bags. The liquid waste drips from the perforated bags onto a preheating subsystem and the solid waste remains in the perforated bags. The preheating subsystem heats up the liquid waste to a pre-disinfection temperature. Finally, steam may be utilized to heat up the liquid waste and the solid waste to a disinfecting temperature.

10 Claims, 15 Drawing Sheets

(56) References Cited

U.S. PATENT DOCUMENTS

| | | | |
|---|---|---|---|
| 8,795,470 B2 * | 8/2014 | Henderson | E04B 1/74 162/141 |
| 2011/0056952 A1 * | 3/2011 | Borowski | B65F 1/0006 220/495.06 |
| 2011/0101137 A1 * | 5/2011 | Langston | B02C 23/18 241/25 |
| 2011/0238598 A1 * | 9/2011 | Borowski | G06Q 99/00 705/500 |
| 2013/0041041 A1 * | 2/2013 | Chandrasekhar | A61L 2/12 514/723 |
| 2013/0306763 A1 | 11/2013 | Carmel | |
| 2014/0040165 A1 * | 2/2014 | Borowski | G06Q 99/00 705/500 |

* cited by examiner

INFECTIOUS WASTE TREATMENT SYSTEM

CROSS REFERENCE TO RELATED APPLICATION

This application claims the benefit of priority from U.S. Provisional Patent Application Ser. No. 62/260,486, filed on Nov. 28, 2015, and entitled "INFECTIOUS WASTE STERILIZING SYSTEM," which is incorporated by reference herein in its entirety.

TECHNICAL FIELD

The present disclosure generally relates to infectious waste treatment, and particularly to a method and apparatus for infectious waste treatment.

BACKGROUND

Hospitals, health-care centers, laboratories and other facilities generate a large amount of infectious waste daily and disposal of this infectious waste poses a major problem. The volume of infectious waste which must be disposed of is increasing and there is a need for a system or apparatus which can accomplish the safe, efficacious, and cost effective treatment of significant volumes of infectious waste.

There is also a need in the art, for a system and apparatus for infectious waste treatment which can reduce the human exposure to infectious waste. Moreover, there is also a need in the art for a system that may provide an effective means for simultaneously and effectively disinfecting solid and liquid wastes.

SUMMARY

The following brief summary is not intended to include all features and aspects of the present application, nor does it imply that the application must include all features and aspects discussed in this summary.

In one general aspect, the present disclosure describes an apparatus for infectious waste treatment. The apparatus may include an inlet subsystem that may have an inlet opening, which may be sized to receive an infectious waste, a shredding subsystem that may be positioned to receive the infectious waste from the inlet subsystem, where the shredding subsystem may include a blade assembly that may be configured for shredding the waste to small particle size, a packaging subsystem that may include a rotatable feeding tray that may have a plurality of openings thereon and a number of perforated bags that may be attached under the respective openings, where, the feeding tray may be configured to rotate the perforated bags and position them to receive the shredded waste therein, and a disinfecting subsystem that may be configured for disinfecting the infectious waste that is packed in the perforated bags, where the disinfecting subsystem may include a main chamber housing the packaging subsystem. The main chamber may have an inlet steam conduit that may be configured to introduce steam into the main chamber. The steam may heat up the waste that is packed inside the perforated bags to a disinfecting temperature.

In another general aspect, the present disclosure relates to a method for infectious waste treatment. The infectious waste may be a mixture of infectious solid waste and infectious liquid waste. The method may include the steps of first, shredding the infectious waste to obtain a mixture of liquid waste and shredded solid waste, filling a plurality of perforated waste bags with the mixture of the liquid waste and the shredded solid waste, where the liquid waste drips from the perforated bags and the solid waste remains in the perforated bags, preheating the liquid waste; and heating up the liquid waste and the solid waste to a disinfection temperature. The liquid waste and the solid waste reach a disinfection temperature simultaneously.

The above mentioned general aspects may include one or more of the following features. The apparatus may further include a preheating subsystem. The liquid waste may drip from the perforated bags onto the preheating subsystem, and the preheating subsystem may include a preheat chamber and a bottom tray that may be positioned immediately over the preheat chamber and may be configured for receiving the liquid waste. The preheat chamber may be filled with steam and is configured to heat up the liquid waste to a pre-disinfection temperature. In one implementation, the pre-disinfecting temperature is in a range of about 90° C. to about 110° C.

According to some implementations, the inlet subsystem may further include an inlet chamber that may be configured to open down to the shredding subsystem. In other implementations, the inlet subsystem may further include a pushing mechanism configured to push down the received infectious waste onto the shredding subsystem.

According to an implementation, the blade assembly may include a plurality of rotatable blade sets that may be mounted on a plurality of shafts that may be positioned horizontally and parallel to one another. The rotatable blade sets may rotate in vertical planes which are substantially parallel to the vertical flowpath of the infectious waste.

According to one implementation, the blade assembly may include two upper blade sets and two lower blade sets. The upper blade sets may be configured to be opposingly rotatable, and the lower blade sets may be configured to be opposingly rotatable.

BRIEF DESCRIPTION OF THE DRAWINGS

While the specification concludes with claims particularly pointing out and distinctly claiming the subject matter that is regarded as forming the present application, it is believed that the application will be better understood from the following description taken in conjunction with the accompanying DRAWINGS, where like reference numerals designate like structural and other elements, in which:

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

For purposes of explanation, specific nomenclature is set forth to provide a thorough understanding of the present disclosure. However, it will be apparent to one skilled in the art that these specific details are not required to practice the principle consistent with the present disclosure. Descriptions of exemplary emboiments are provided only as representative examples. Various modifications to the exemplary embodiments will be readily apparent to one skilled in the art, and the general principles defined herein may be applied to other implementations and applications without departing from the scope of the principles of the present disclosure. The present disclosure is not intended to be limited to the implementations shown, but is to be accorded the widest possible scope consistent with the principles and features disclosed herein.

Described in this disclosure is a system and apparatus for infectious waste treatment. The system as described according to several aspects of the present disclosure may be suited for the treatment of infectious waste generated by hospitals and other medical facilities. Such infectious wastes may include plastic, paper, fabric, glass, and metal and they may embody a broad range of medical items, such as syringes, bottles, tubes, dressings, and the like. The infectious waste may be a mixture of solid and liquid waste. The term infectious waste treatment, as used herein, may constitute shredding the infectious waste into relatively smaller fragments and disinfecting the shredded waste to render it substantially innocuous and suitable for ordinary landfilling. The system and apparatus of the present disclosure may provide means for receiving the infectious waste packed in waste bags and delivering disinfected wastes in special packages after shredding and disinfecting the received waste, thus reducing human exposure to the infectious waste.

Figure 1:
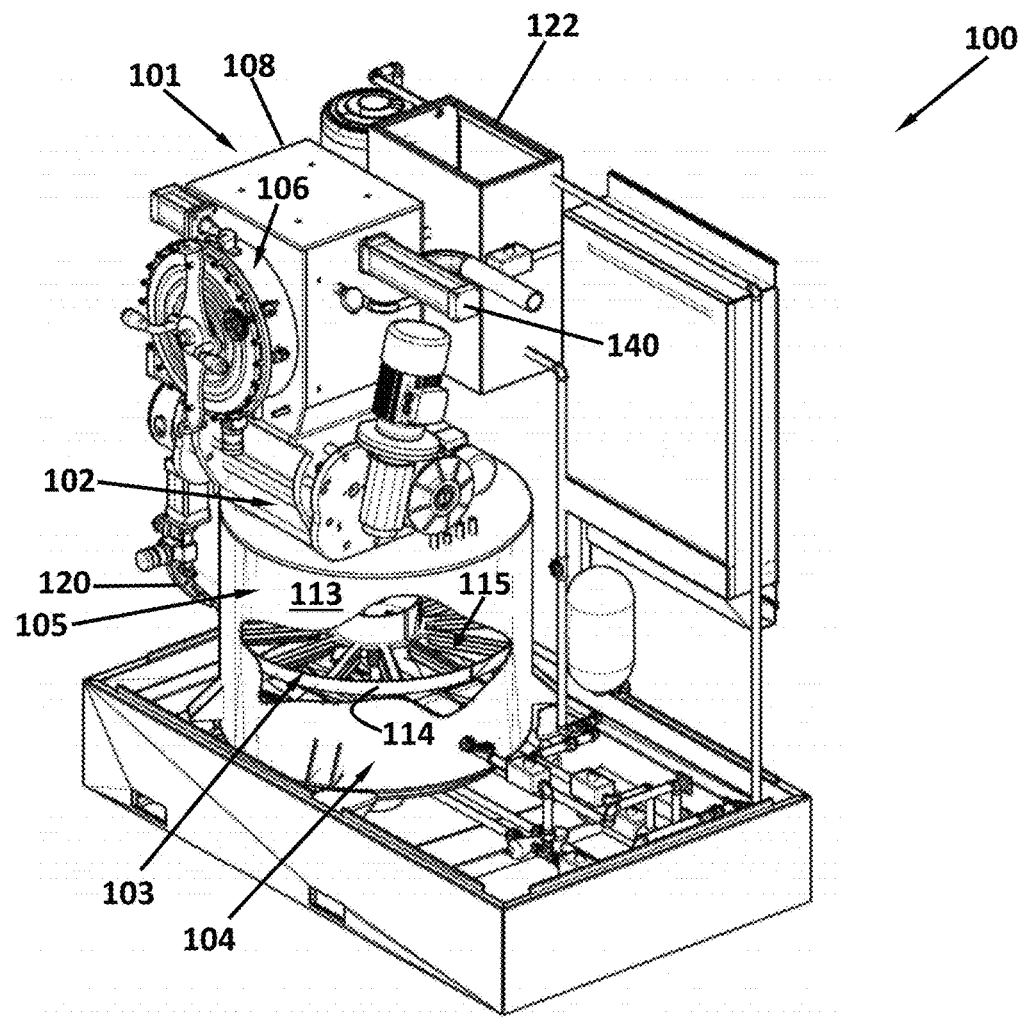
FIG. 1 is a perspective view of an exemplary infectious waste treatment system, consistent with one or more exemplary embodiments of the present disclosure.
Figure 2:
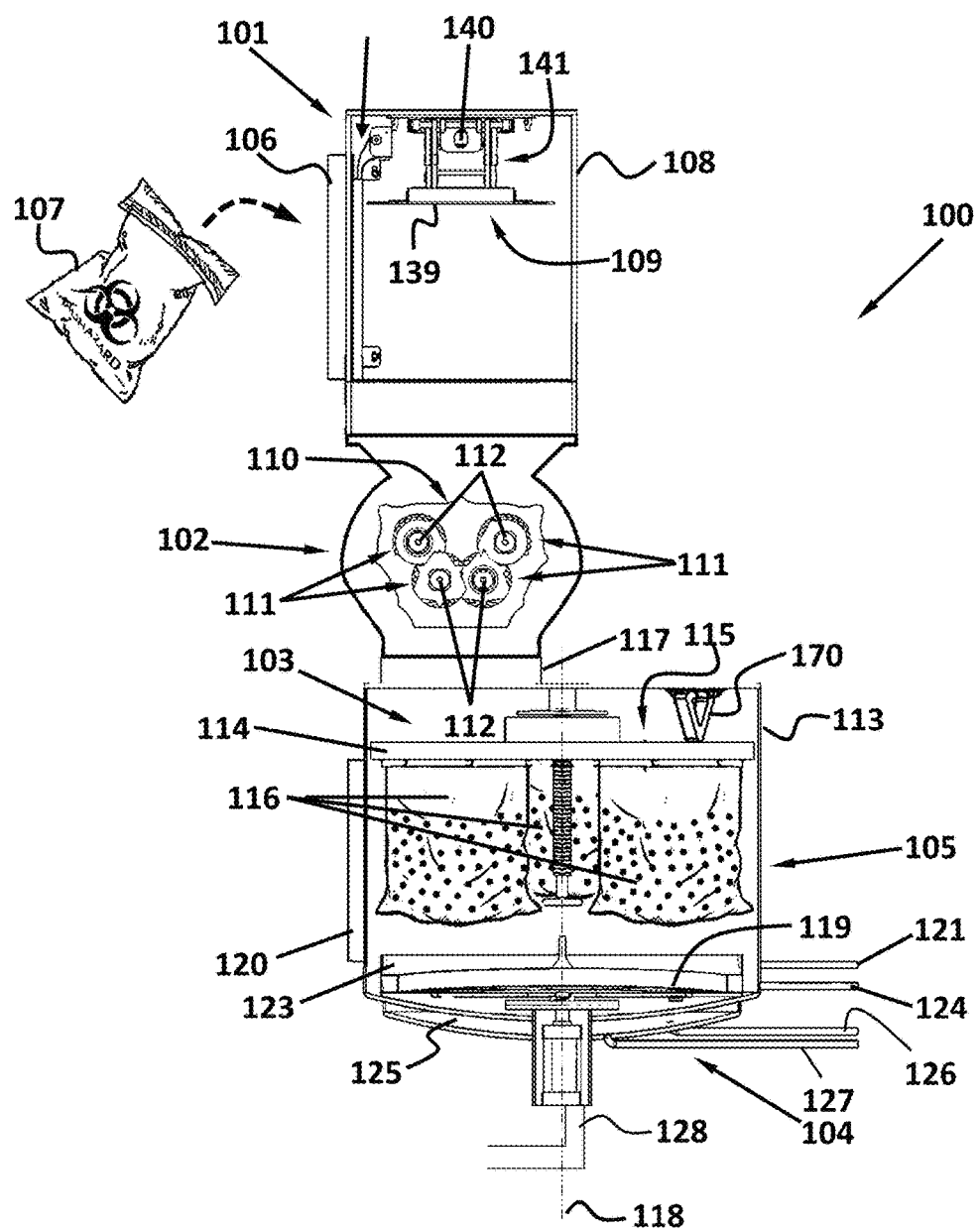
FIG. 2 is a schematic view of the system of FIG. 1.

Referring to FIGS. 1 and 2, an exemplary implementation of an infectious waste treatment system 100, consistent with one or more exemplary embodiments of the present disclosure may include a number of subsystems, namely, an inlet subsystem 101, a shredding subsystem 102, a packaging subsystem 103, a preheating subsystem 104, and a disinfecting subsystem 105.

The inlet subsystem 101 may include an inlet opening 106, through which an operator may feed infectious waste into the infectious waste treatment system 100. In an exemplary implementation, however, the infectious waste may be stored in an infectious waste bag 107, which may be fed through the inlet opening 106 into the system 100 in its entirety. The inlet subsystem 101 may include an inlet chamber 108 that may open down into the shredding subsystem 102. The infectious waste may drop down into shredding subsystem 102 under the force of gravity, however, in an exemplary implementation, the inlet subsystem 101 may further include a pushing mechanism 109 that may be configured to push down the infectious waste received through the inlet opening 106 onto the shredding subsystem 102.

The shredding subsystem 102 may include a blade assembly 110 having a number of rotatable blade sets 111 that may be mounted on a number of blade shafts 112 configured with an arrangement that will be described in detail later in this disclosure. The shredding subsystem 102 may be configured for shredding all types of infectious waste into a selected particle size.

The packaging subsystem 103, may be provided immediately downstream from shredding subsystem 102 inside a main chamber 113. Packaging subsystem 103 may include a rotatable feeding tray 114 having a number of openings 115 thereon and a number of perforated bags 116 removably attached under the rotatable feeding tray 114 and positioned immediately under respective openings 115 such that an upper opening of each bag is aligned with a corresponding opening on the feeding tray 114. The shredded waste falls down from the shredding subsystem 102 through shredded waste passage 117 onto the feeding tray 114 into the perforated bag 102 that is positioned under the waste passage 117. The feeding tray 114 may be rotatable about the central axis 118 of the main chamber 113, thereby rotating the perforated bags 116 under shredded waste passage 117 through which shredded waste pours down onto the feeding tray 114 and into the perforated bags 116 until all perforated bags 116 are filled with shredded waste. The infectious liquid medium of the shredded waste may drip from the perforations on the perforated bags 116 onto a bottom tray 119 that may be positioned under the perforated bags 116 and may be configured to collect the infectious liquid medium.

The main chamber 113 may include an access door 120 that may be used by an operator in order to, for example attach the perforated bags 116 under the rotatable feeding tray 114 or detaching the bags 116 once the disinfection cycle is finished. Once all the perforated bags 116 are full of shredded infectious waste, the inlet opening 106 and the access door 120 may be closed, thereby sealing the entire inlet subsystem 101, shredding subsystem 102 and the main chamber 113 for subsequent steam disinfection of the infectious waste inside the perforated bags 116. Superheated steam with temperature ranging from about 121° C. to about 134° C. may be introduced into the main chamber 113 via steam supply piping that may be connected to a steam inlet conduit 121. The elevated temperature of steam may cause the infectious waste to heat up to a disinfection temperature. The infectious waste may be heated for a period of approximately, for example 30 minutes, this period is herein referred to as the disinfection cycle. The introduced steam may fill the air spaces within the inlet subsystem 101, the shredding subsystem 102 and the main chamber 113 and it may disinfect the contents of these subsystems. Once the contents of the system 100 have been disinfected, the steam may be discharged and the inlet opening 106 and the access door 120 may then be opened. The perforated bags 116 and their content may be removed via the access door 120. The steam may be discharged into a condensate vessel 122 and after condensation, the condensate may be drained to sewer system. During the disinfection cycle, where steam may be introduced to the system, a small portion of the steam may condense and the condensate may drip down the walls of the inlet subsystem 101, the shredder subsystem 102 and the main chamber 113. This condensate may be collected by a steam trap 123 that may be positioned at the bottom of the main chamber 113 mounted coaxially around the bottom tray 119. The condensate may exit the chamber 113, once the disinfection is finished, through a condensate drain 124 to the sewer system.

Referring to FIG. 2, the system 100 may further include a preheating subsystem 104 that may be configured for preheating the infectious liquid medium that has dripped down the perforated bags 116 onto the bottom tray 119. The preheating subsystem 104 may include a preheat chamber 125 that may be positioned at the bottom of the system 100 immediately under the bottom tray 119. The preheat chamber 125 may include a steam inlet 126 and an outlet 127. The temperature of the preheat chamber 125 may be maintained at 90° C. to about 110° C. The preheating subsystem 104 may be configured to preheat the infectious liquid medium prior to the disinfection cycle. The temperature of the infectious solid waste inside the perforated bags 116 increases with higher rate compared to the temperature of the infectious liquid medium on the bottom tray 119, therefore, solid waste in the perforated bags 116 may reach the disinfection temperature sooner, in order for the solid and liquid waste to reach the disinfection temperature at a same time, the liquid medium on the bottom tray 119 may be preheated by the preheating subsystem 104 to a temperature of approximately 90° C. to about 110° C. This way, when the superheated steam is introduced to the system 100 during the disinfection cycle, the solid and liquid wastes may reach the disinfection temperature at a same time. After the disinfection cycle, the liquid medium may be drained to the sewer system via a drain 128. Steam may be introduced into the preheat chamber 125 via the steam inlet 126 and it may be discharged through the outlet 127.

Figure 3A:
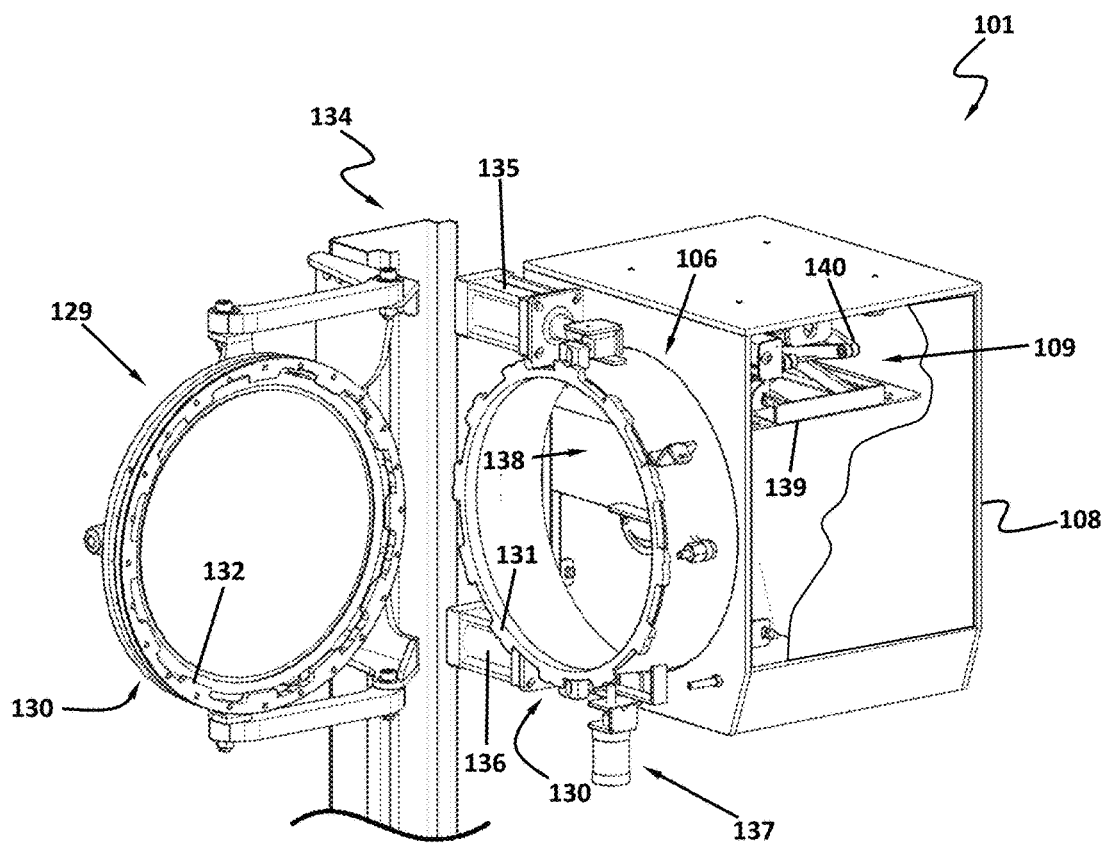
FIGS. 3A and 3B illustrate example implementations of an inlet subsystem, consistent with one or more exemplary embodiments of the present disclosure.
Figure 3B:
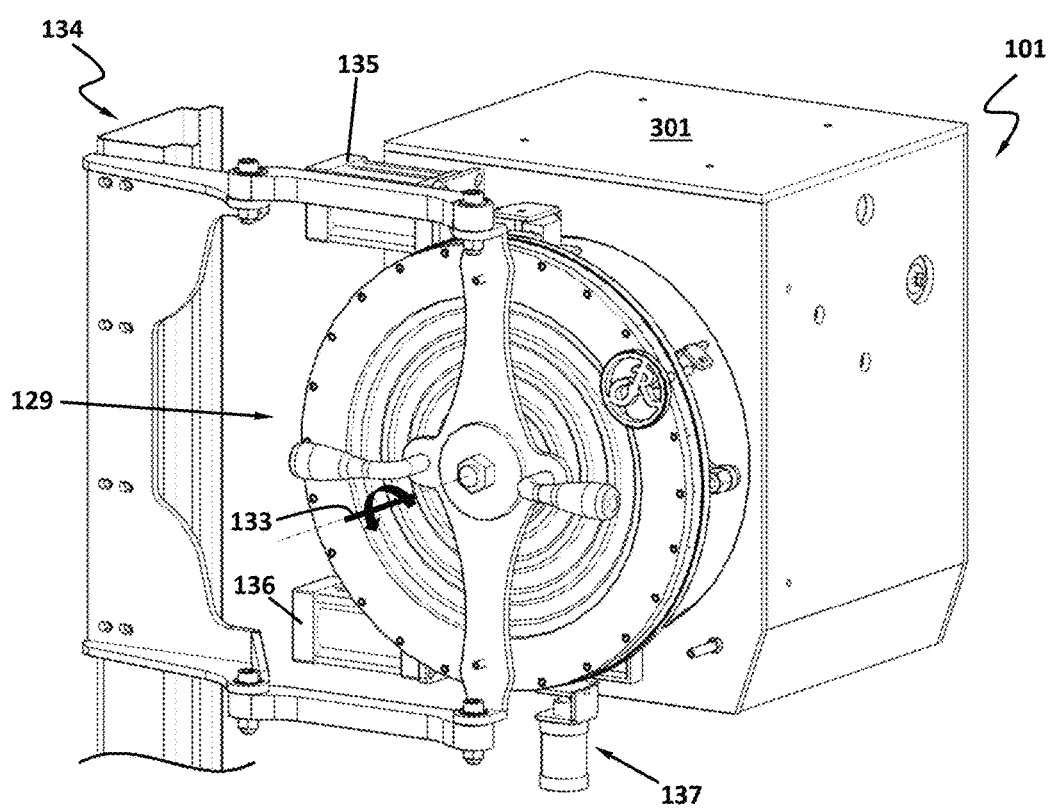
Figure 3C:
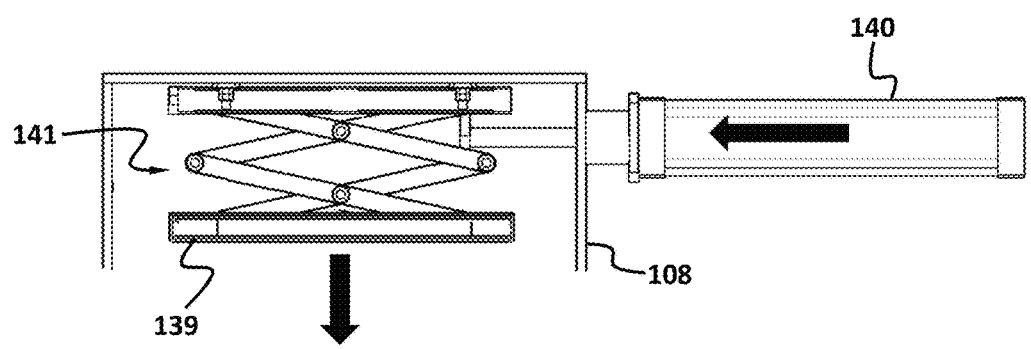
FIG. 3C is a schematic of an example of a pushing mechanism, consistent with one or more exemplary embodiments of the present disclosure.

FIG. 3A illustrates an example implementation of the inlet subsystem 101 and a pressure door 129 that may be utilized to seal the inlet opening 106 in a situation where the pressure door 129 is open and FIG. 3B illustrates the same example implementation of the inlet subsystem 101, with the pressure door 129 closed, consistent with one or more exemplary embodiments of the present disclosure. Referring to FIGS. 3A and 3B, the inlet chamber 108 may be structured as an enclosure made up of, for example, steel plates that may be capable of withstanding high pressures during the disinfection cycle.

Referring to the implementation shown in FIGS. 3A and 3B, the inlet opening 106 may be configured to be sealed by the pressure door 129 with an interlocking mechanism that can keep the pressure door 129 locked while the pressure of the system is above atmospheric pressure. In one implementation, a teeth locking mechanism 130 may be used for sealing the pressure door 129. The teeth locking mechanism 130 may include a first set of teeth 131 attached around the circumference of the inlet opening 106 and a second set of teeth 132 attached to the pressure door 129. The pressure door 129 may be closed and then it may be rotated about its normal axis 133 until the first set of teeth 131 lock with the second set of teeth 132 and the inlet opening 106 can be sealed tightly under working pressure. The pressure door 129 may be mounted on a chassis 134 near the inlet opening 106.

According to the exemplary implementation shown in FIG. 3B, the pressure door 129 may include, for example two pneumatic jacks 135, 136 that may be attached above and under the pressure door 129. The pressure door 129 may be closed, and once the pressure door 129 is closed, the two pneumatic jacks 135, 136 may drive a rotational movement of the pressure door 129 about axis 133, thereby locking the first and second set of teeth 131, 132 into one another.

Referring to FIG. 3B, in an examplary implementation, an interlock 137 may be provided under the inlet opening 106, preventing the pressure door 129 from opening during the disinfection cycle. The interlock 137 may be attached to the inlet opening 106. The interlock 137 may include a spring, a piston and a cylinder. When the inner pressure of the inlet chamber 108 is high, the vapor may enter the interlock cylinder, pressing the spring and pushing the piston forward. The piston is pressed to, for example pneumatic jack 136, thus preventing the pneumatic jack 136 from moving and opening the pressure door 129.

Referring to FIGS. 1 and 3A, the inlet subsystem 101 may further include a safety door mechanism 138. The safety door mechanism 138 may serve primarily as a mechanical barrier preventing the exit of waste material fragments from the inlet chamber 108. In an exemplary implementation, the safety door mechanism 138 may be configured as a roller door attached to the top inner part of the inlet chamber 108. The safety door 138 may be pulled down and thereby close the inlet opening 106 during the shredding process to prevent the exit of waste material fragments, and to provide safety for the operator. The safety door 138 may be configured such that only when it is closed the shredding system works.

According to the exemplary implementations shown in FIGS. 1, 2, and 3A, the pushing mechanism 109 may be provided in the inlet chamber 108 and may be configured for pushing the infectious waste onto the shredding subsystem 102. The pushing mechanism 109 may be attached to the top inner side of the inlet chamber 108. According to an exemplary implementation, once the infectious waste is loaded into the inlet chamber 108, and the safety door 138 is closed, the pushing mechanism 109 moves down, pushing the infectious waste onto the shredding subsystem 102 and preventing leftovers inside the inlet chamber 108. In the exemplary implementation shown in FIGS. 1, 2, 3A and 3C, the pushing mechanism 109 may include a pushing plate 139, a pneumatic jack 140, and it may be configured with a scissor mechanism 141. During the shredding process the horizontal movement of the pneumatic jack 140 may be converted into a substantially vertical movement of the scissor mechanism 141 and the pushing plate 139 attached thereto. It should be known by a person skilled in the art, through reading this disclosure, that any other actuating mechanism may be used for pushing the plate 130 onto the waste bags and force them down onto the shredding subsystem 102.

Figure 4A:
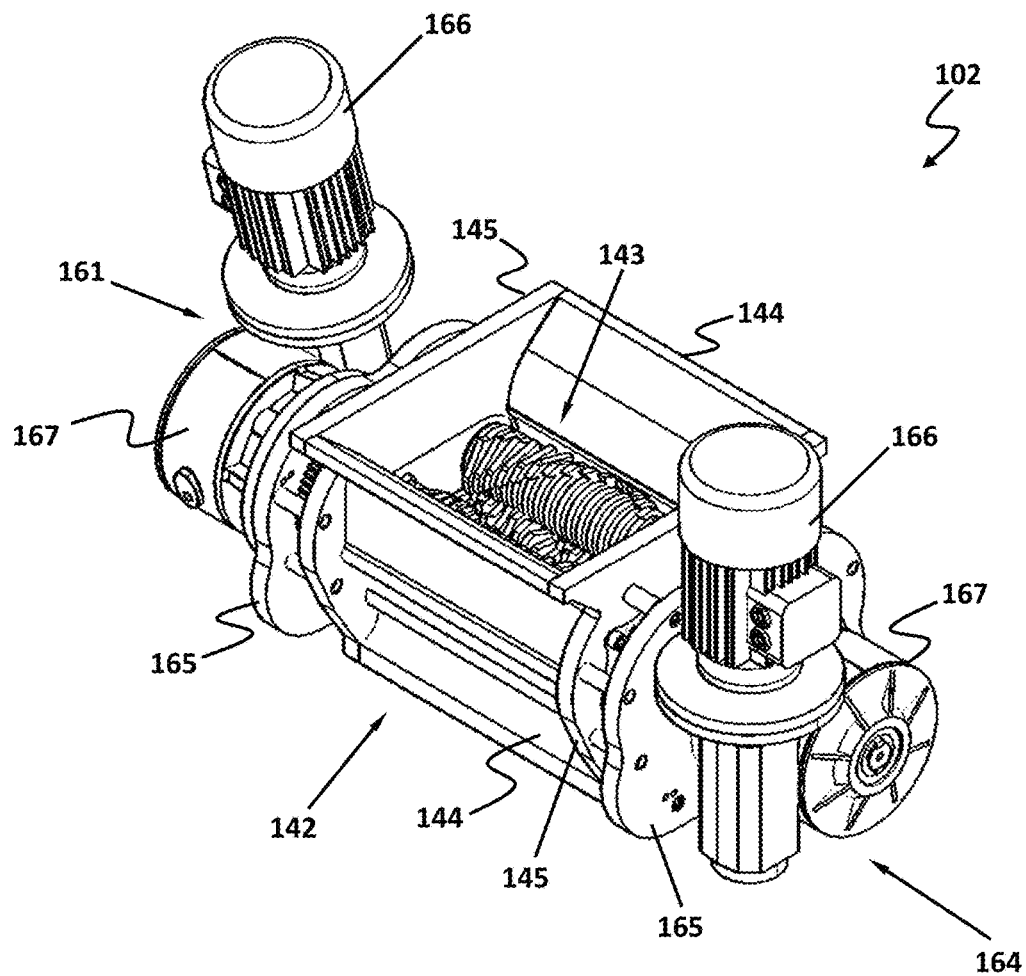
FIG. 4A is a perspective view of an exemplary shredding subsystem, consistent with one or more exemplary embodiments of the present disclosure.

FIG. 4A illustrates a perspective view of an example implementation of the shredding subsystem 102. According to the implementation shown in FIG. 4A, the shredding subsystem 102 may include a main body 142 and a blade assembly 143 mounted therein. In an exemplary implementation, the main body 142 may include two sloped side walls 144 and two end blocks 145. The sloped side walls 144 may be structured and configured for guiding the waste down into the blade assembly 143 to be shredded into smaller fragments.

Figure 4B:
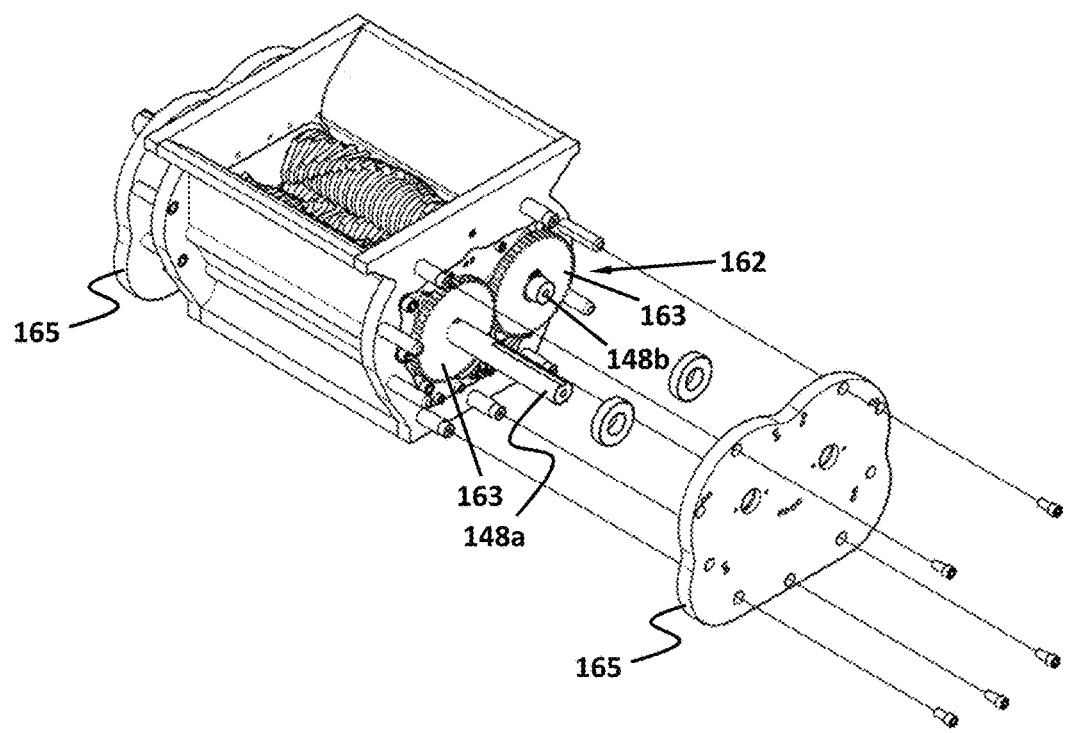
FIG. 4B is an exploded view of an exemplary shredding subsystem, consistent with one or more exemplary embodiments of the present disclosure.
Figure 4C:
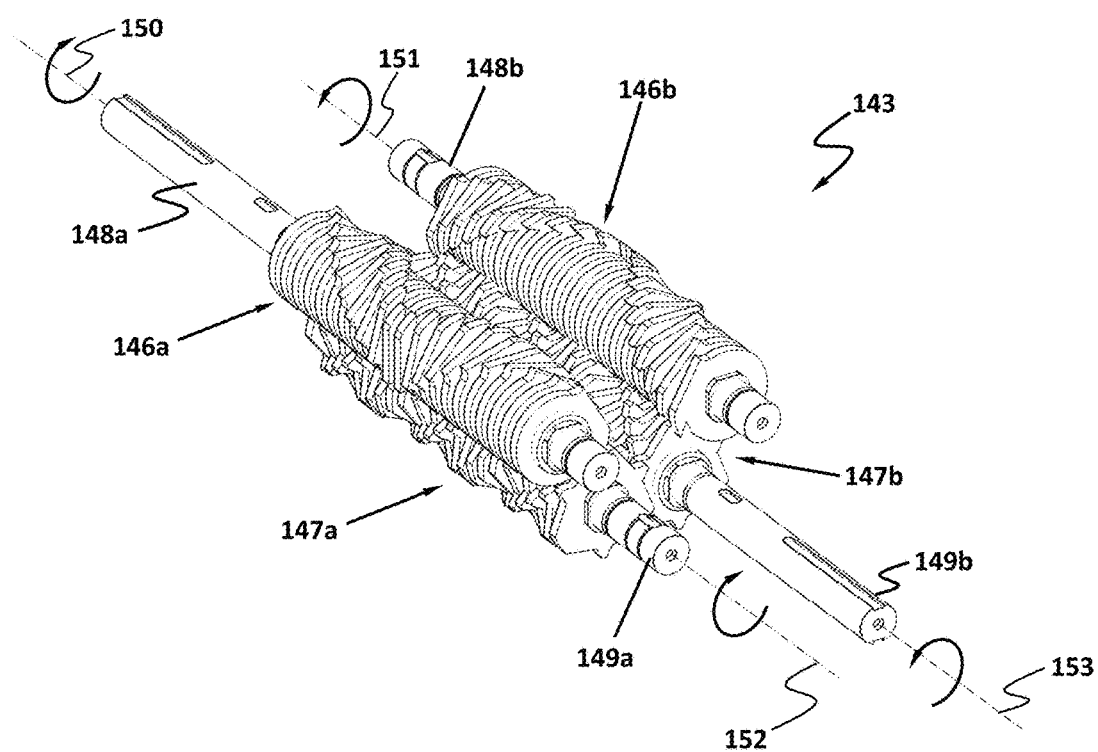
FIG. 4C illustrates an exemplary blade assembly, consistent with one or more exemplary embodiments of the present disclosure.

According to FIG. 4C, the blade assembly 143 may include a number of rotatable blade sets 146a, 146b, 147a, and 147b mounted on a number of shafts 148a, 148b, 149a, and 149b, respectively. The shafts 148a, 148b, 149a, and 149b may be supported on the end blocks 145 and may be positioned horizontally and parallel to one another, and the rotatable blade sets 146a, 146b, 147a, and 147b may rotate in vertical planes which are substantially parallel to the vertical flowpath of the infectious waste.

Referring to the exemplary implementation shown in FIG. 4C, the blade assembly 143 may include two upper blade sets 146a and 146b and two lower blade sets 147a and 147b mounted on two corresponding upper shafts 148a and 148b and two corresponding lower shafts 149a and 149b. The upper shafts 148a and 148b may be configured to be opposingly rotatable inwardly about axes 150 and 151, and the lower shafts 149a and 149b may be configured to be opposingly rotatable inwardly about axes 152 and 153. The upper shafts 148a and 148b and lower shafts 149a and 149b may rotate inwardly in order to pull the waste inwardly between the blade sets 146a, 146b, 147a, and 147b.

Figure 4D:
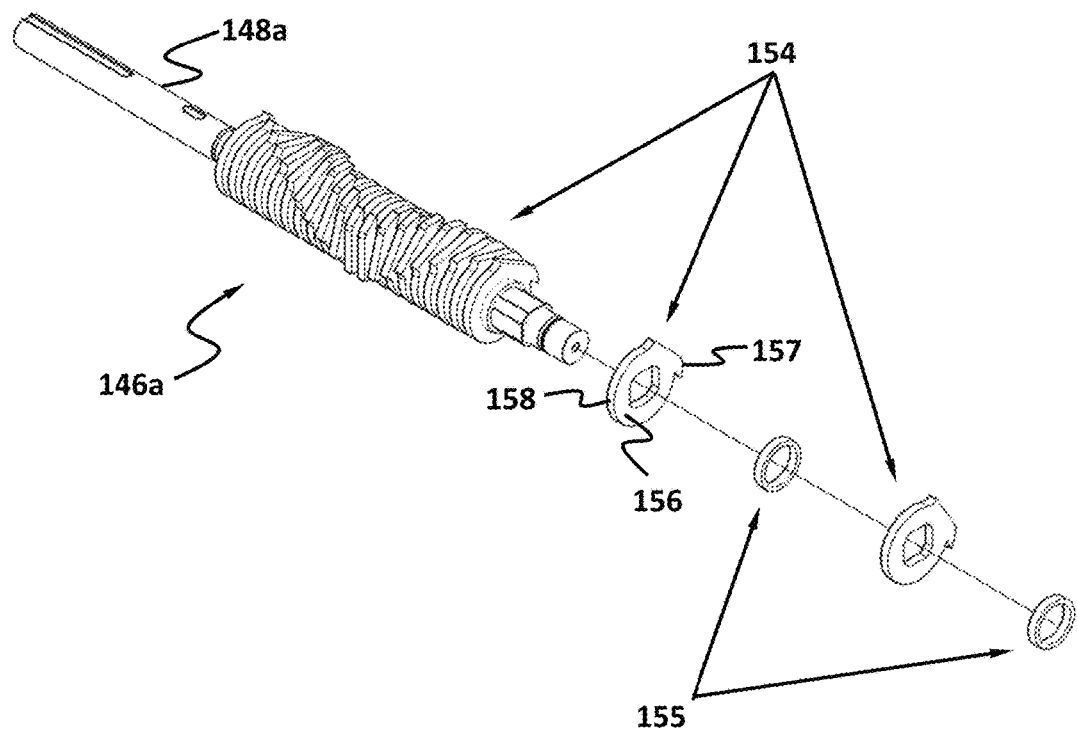
FIG. 4D illustrates an example of an upper shredding blade set, consistent with one or more exemplary embodiments of the present disclosure.
Figure 4E:
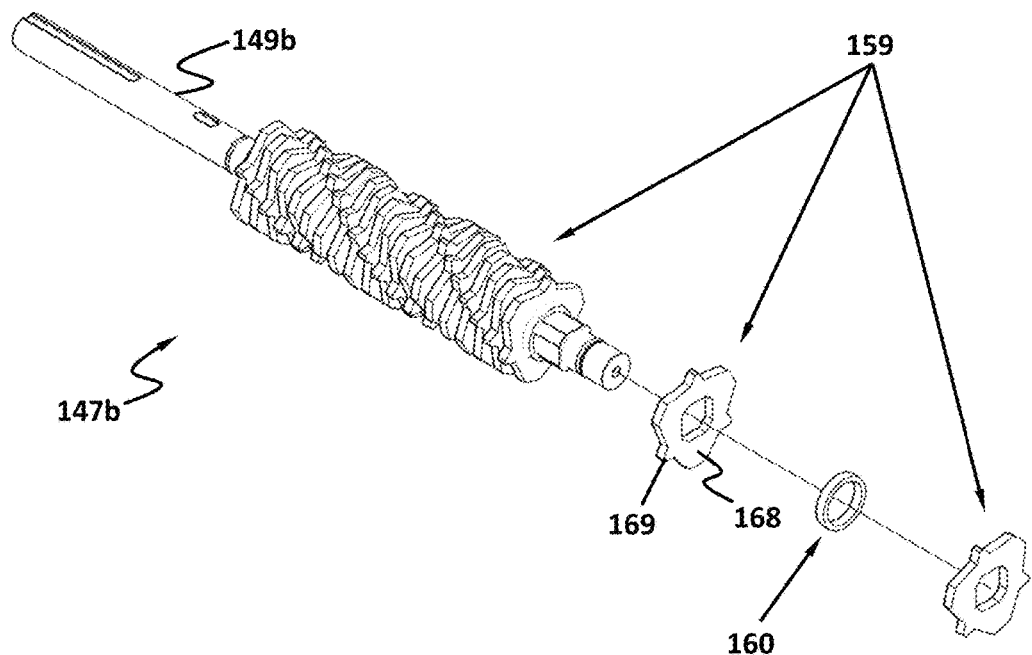
FIG. 4E illustrates an example of a lower shredding blade set, aconsistent with one or more exemplary embodiments of the present disclosure.

Referring to FIG. 4D, each upper blade set, for example, blade set 146a may include a number of shredding blades 154 that may be rotatably mounted on shaft 148a appropriately spaced apart using circular spacers 155 therebetween. Referring to FIG. 4E, each lower blade set, for example blade set 147b may include a number of shredding blades 159 that may be rotatably mounted on each lower shaft, for example shaft 148b appropriately spaced apart using circular spacers 160 therebetween. According to an exemplary implementation, the lower shredding blades 159 and the upper shredding blades 154 may be configured with different shapes.

In the exemplary implementation shown in FIG. 4D, each rotatable shredding blade 154 may be configured as a disk 156 having a number of teeth 157 about the periphery 158 of disk. Referring to FIG. 4E, according to another exemplary implementation, each rotatable shredding blade 159 may be configured with a triangular shape 168 having a number of teeth 169 about the periphery of each blade 159. According to other exemplary implementations, the lower shredding blades 159 and the upper shredding blades 154 may be configured with similar shapes of teeth with various configurations. The upper rotatable blade sets 146a and 146b may be configured to shred an infectious waste bag into small fragments with a first particle size and the lower rotatable blade sets 147a and 147b may be configured to shred the fragments with the first particle size into fragments with a second and smaller particle size.

Referring to FIGS. 4A and 4B, in an exemplary implementation one of the upper shafts, for example, upper shaft 148a may be configured with a longer length and it may be coupled to a rotary actuator 161. The actuator 161 may drive a roll rotation of the shaft 148a about its longitudinal axis and shaft 148a may be coupled to shaft 148b with a gear system 162 having two gears 163, one tightly mounted on shaft 148a, and the other tightly mounted on shaft 148b, rotational movement of shaft 148a may be transferred via the gear system 162 to shaft 148b. A similar configuration may be used for lower shafts 149a and 149b. The lower shafts 149a, 149b may be coupled to another rotary actuator 164. In some exemplary implementations, each rotary actuator 161, 164 may include a motor 166 and a gearbox 167 coupled with one of the shafts from each side. According to other exemplary implementations, two mounting members 165 may be utilized at either sides of the shredding subsystem 102 to mount the rotary actuators 161 and 164 on the shredding subsystem 102.

Figure 5A:
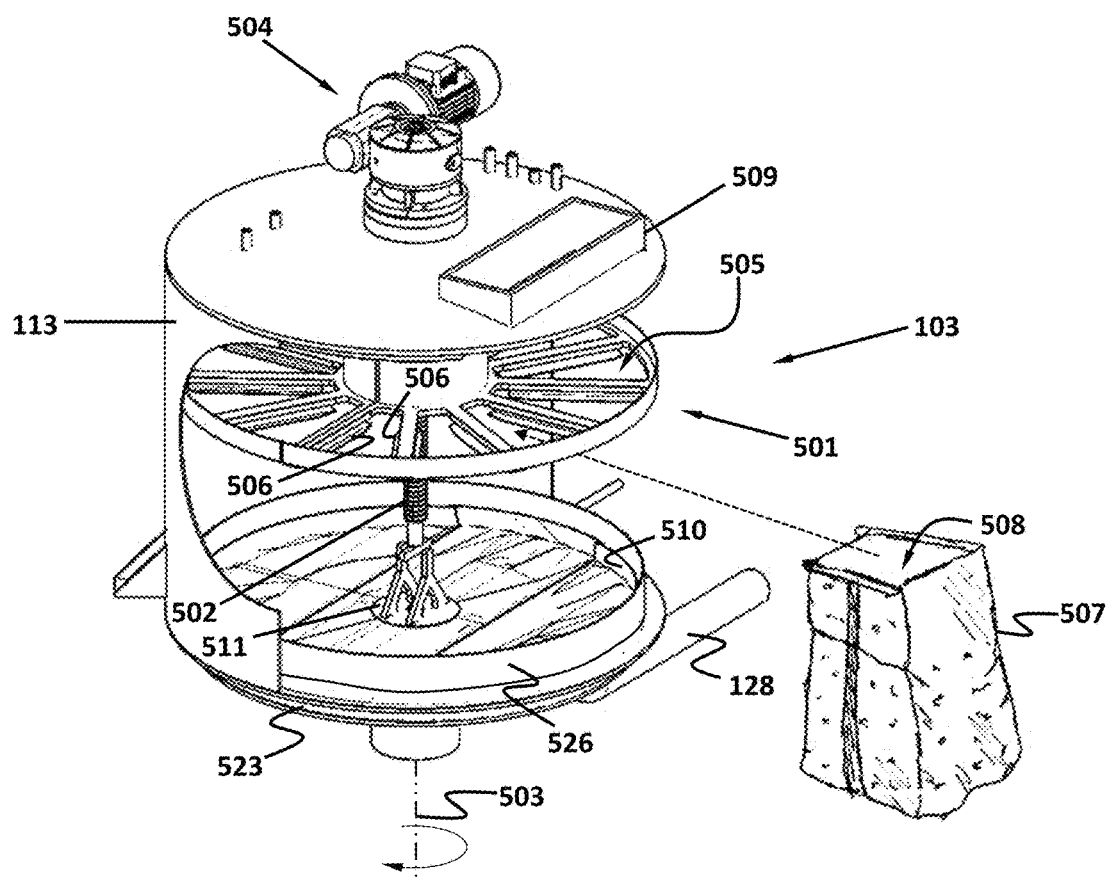
FIGS. 5A and 5B, illustrate examples of a packaging subsystem, consistent with one or more exemplary embodiments of the present disclosure.
Figure 5B:
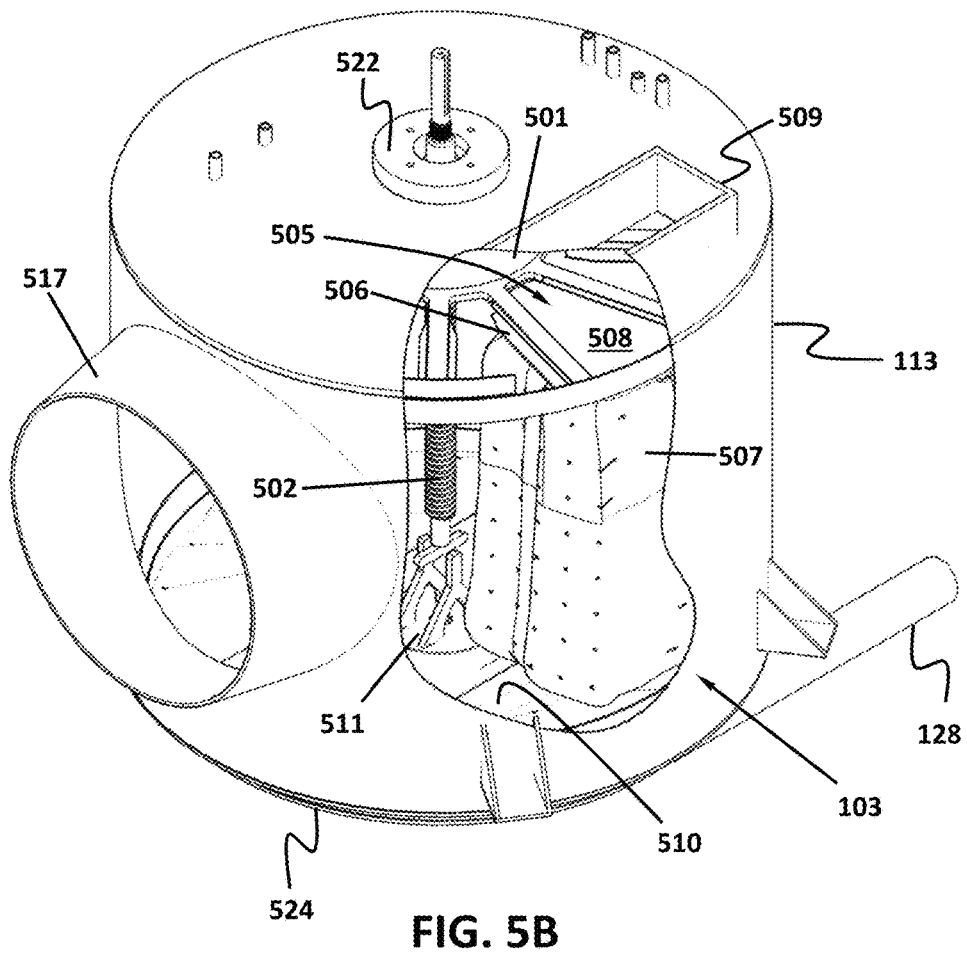

FIGS. 5A and 5B illustrate exemplary implementations of packaging subsystem 103 housed in the main chamber 113. The packaging subsystem 103 may include a rotatable feeding tray 501 (an implementation of feeding tray 114 of FIGS. 1 and 2) mounted on a main shaft 502. The main shaft 502 may be coupled to a rotary actuator 504 and the rotary actuator 504 and the main shaft 502 may be configured to drive a rotational movement of the rotatable feeding tray 501 about central vertical axis 503 of the main chamber 113. The rotatable feeding tray 501 may have a number of openings 505 thereon. Referring to the implementation shown in FIGS. 5A and 5B, the openings 505 may be pie-shaped openings having attachment means 506 configured for removably attach a number of perforated waste bags 507 (only one waste bag 507 is shown herein) thereto. Each perforated waste bag 507 may be removably attached under each pie-shaped opening 505 such that the upper opening 508 of each perforated bag 507 is aligned with each pie-shaped opening 505. In an implementation, each waste bag 507 may be slidably attached under each pie-shaped opening 505. In an aspect, as the feeding tray 501 rotates about axis 503, and rotates the perforated bags 507 under shredded waste passage 509 one by one and shredded waste falling down from the shredding subsystem 102 falls into perforated bags 507. The perforated waste bags 507 attached under the openings 505 of the feeding tray 501 may sit on a bottom tray 510 that is placed immediately under the perforated waste bags 507 coaxial with the feeding tray 501 and rotatable therewith. The bottom tray 510 may be coupled to the main shaft 502 via a coupling means 511 and be rotatable therewith. As the shredded infectious waste, which may be a mixture of solid and liquid waste pours into the perforated bags 507 as they constantly rotate under the shredded waste passage 509, the liquid waste poured into the bags 507 may drip from the perforations on the perforated waste bags 507 onto the bottom tray 510. The bottom tray 510 may be configured to collect the dripped liquid waste. The solid waste may remain in the perforated bags 507 and the liquid waste is collected on the bottom tray 510. In an exemplary aspect, once all the perforated waste bags 507 are fully filled with shredded waste, the disinfection cycle may begin. In an implementation, a sensing mechanism 170 (numbered in FIG. 2) may be used to check if the perforated bags 507 are fully filled with shredded waste. Referring to FIG. 2, the sensing mechanism 170 may be placed above the feeding tray 114 under the top inner part of the main chamber 113.

Figure 6A:
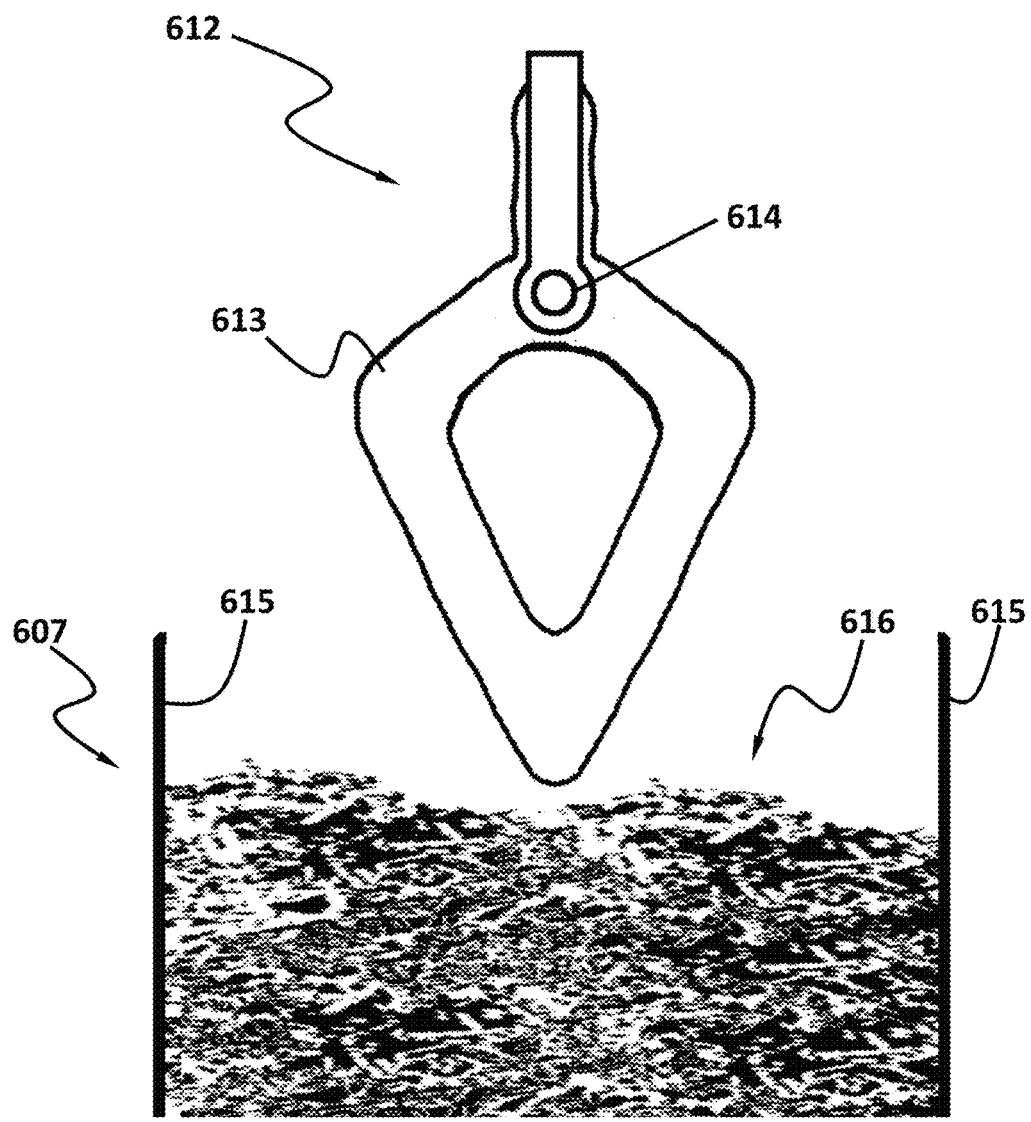
FIGS. 6A and 6B are schematics of a sensing mechanism, consistent with one or more exemplary embodiments of the present disclosure.
Figure 6B:
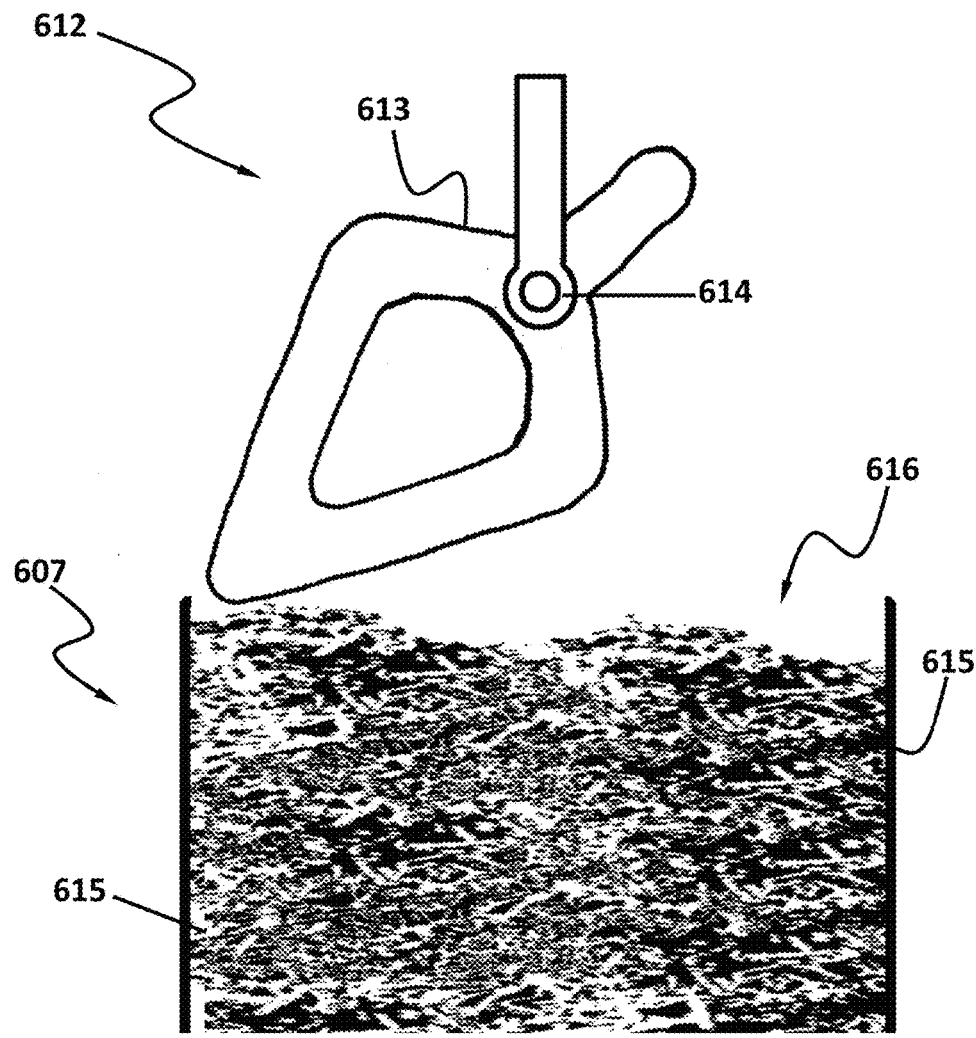

Referring to FIG. 6A, the sensing mechanism 612 may have a pivoting member 613 that may be configured to pivot about point 614. The sensing mechanism 612 may be configured such that any time the member 613 pivots about point 614 and thereby deviates from its default vertical position, an electric pulse is sent by the sensing mechanism 612. When the perforated bags 607 are not fully filled with shredded waste 616 (as in FIG. 6A), the sensing mechanism 612 sends only two pulses per each passing perforated bag 607 corresponding to two edges 615 of the bags 607 pushing the member 613 out of its vertical alignment. Referring to FIG. 6B, once the perforated bags 607 are fully filled with shredded waste 616 the member 613 is forced by the shredded waste to pivot out of its vertical alignment and send a continuous electric signal corresponding to the state where all perforated bags 607 are fully filled with shredded waste.

Figure 5C:
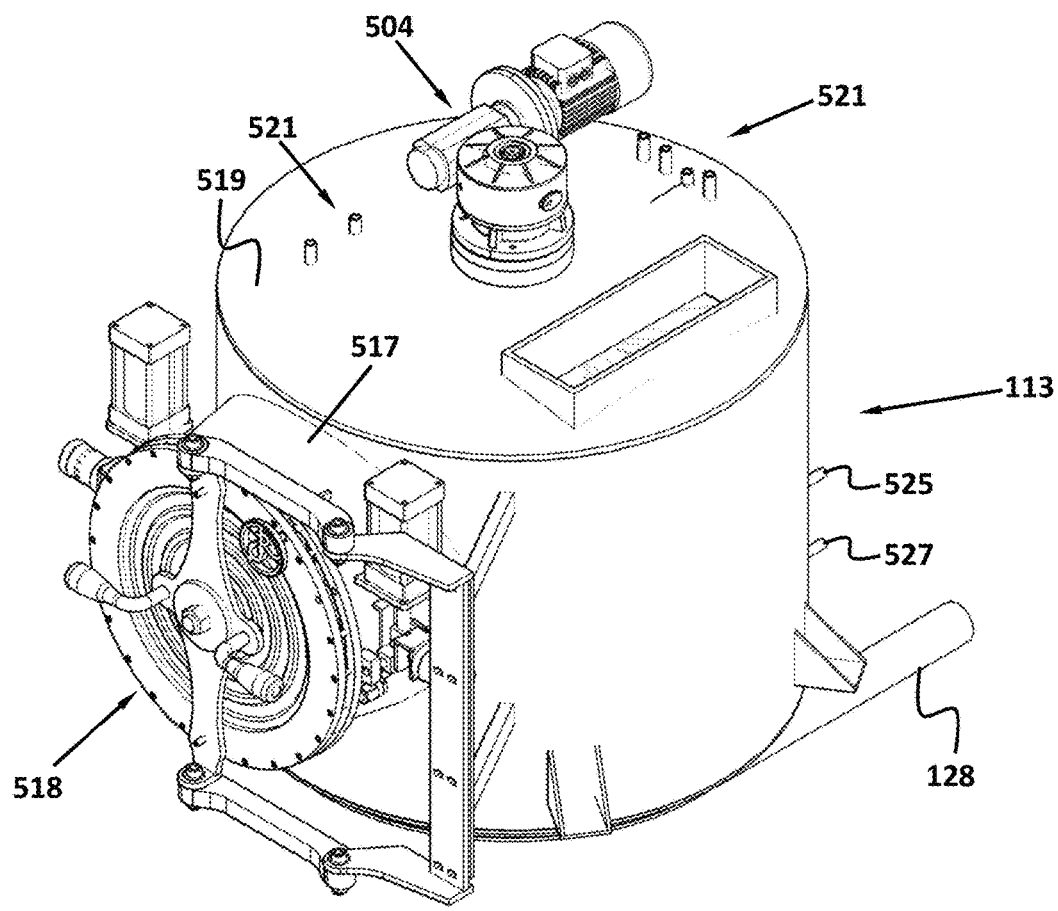
FIG. 5C is perspective view of an example of a main chamber, consistent with one or more exemplary embodiments of the present disclosure.

Referring to the exemplary implementation shown in FIGS. 5B and 5C, the main chamber 113 may include an access door 517 (an implementation of access door 120 of FIG. 2), which may be tightly sealed by a pressure door 518 with a configuration similar to the configuration described for the inlet opening door 129 in FIGS. 3A and 3B. The access door 517 may be configured for providing access to the packaging subsystem 103 inside the main chamber 113. The access door 517 may be used for attaching perforated bags 507 under the feeding tray 501 before the disinfection cycle. Once all the perforated bags 507 are filled with shredded waste and the system is ready to begin the disinfection cycle, the pressure door 518 may be closed and it may provide a steam tight seal for the access door 517. After the infectious cycle is over, the access door 517 may be opened in order to provide access to the perforated bags 507 for removing them from the system. All sensors and switches may enter the system from special openings 521 provided on top cap 519 of the main chamber 113. Rotary actuator 504 may be mounted on the main chamber 113 and it may be coupled to the main shaft 502 via a coupling member 522. Referring to FIG. 5A, preheat chamber 523 (an exemplary implementation of preheat chamber 125 of FIG. 2) may be positioned immediately under the bottom tray 510 over the bottom cap 524 of the main chamber 113 and it may be filled with steam in order to preheat the liquid waste collected on the bottom tray 113 before the disinfection cycle. Referring to FIGS. 5A and 5C, during the disinfection cycle, superheated steam may enter the main chamber 113 via steam inlet conduit 525. The condensed steam near the walls of the system may drip down the walls and a ring-shaped trap 526 coaxially position around the bottom tray 510 may be utilized for collecting this condensed steam, and the collected condensate may exit the main chamber 113 via a condensate drain outlet provided at the bottom of the trap 526. Once the disinfection cycle is over the remaining steam may exit the main chamber 113 via steam outlet 527 to a condensate vessel (visible in FIG. 1 with reference numeral 122). The disinfected liquid waste on the bottom tray 510 may be drained out of the system via drain 128.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

What is claimed is:

1. An apparatus for infectious waste treatment, comprising:
   an inlet subsystem having an inlet opening sized to receive an infectious waste;
   a shredding subsystem positioned to receive the infectious waste from the inlet subsystem, wherein the shredding subsystem includes a blade assembly configured for shredding the infectious waste to small particle size;
   a packaging subsystem comprising a rotatable feeding tray having a plurality of openings thereon and a plurality of perforated bags attached under the respective openings, wherein the rotatable feeding tray is configured to rotate the plurality of perforated bags and position them to receive the shredded infectious waste therein; and
   a disinfecting subsystem configured for disinfecting the infectious waste packed in the plurality of perforated bags, wherein the disinfecting subsystem comprises a main chamber housing the packaging subsystem, having an inlet steam conduit configured to introduce steam into the main chamber.

2. The apparatus according to claim 1, wherein the infectious waste is a mixture of solid waste and liquid waste, wherein the apparatus further comprises a preheating subsystem, wherein the liquid waste drips from the plurality of perforated bags onto the preheating subsystem, wherein the preheating subsystem comprises a preheat chamber and a bottom tray positioned immediately over the preheat chamber and configured for receiving the liquid waste, wherein the preheat chamber is filled with steam and is configured to heat up the liquid waste to a pre-disinfection temperature.

3. The apparatus according to claim 2, wherein the pre-disinfection temperature is in a range of 90° C. to 110° C.

4. The apparatus according to claim 1, wherein the inlet subsystem further comprises an inlet chamber configured to open down to the shredding subsystem.

5. The apparatus according to claim 1, wherein the inlet subsystem further comprises a pushing mechanism configured to push down the received infectious waste into the shredding subsystem.

6. The apparatus according to claim 1, wherein the blade assembly comprises a plurality of rotatable blade sets mounted on a plurality of shafts positioned horizontally and parallel to one another, wherein the rotatable blade sets rotate in vertical planes which are substantially parallel to a vertical flowpath of the infectious waste.

7. The apparatus according to claim 1, wherein the blade assembly includes two upper blade sets and two lower blade sets, wherein the two upper blade sets are configured to be opposingly rotatable, and wherein the two lower blade sets are configured to be opposingly rotatable.

8. The apparatus according to claim 1, wherein the plurality of the perforated bags are removably attached under the plurality of openings of the rotatable feeding tray.

9. The apparatus according to claim 1, wherein the disinfecting subsystem is configured to heat up the infectious waste inside the plurality of perforated bags to a disinfection temperature.

10. The apparatus according to claim 9, wherein the disinfection temperature is in a range of 121° C. to 134° C.

* * * * *